United States Patent [19]

Snoke et al.

[11] 4,316,954
[45] Feb. 23, 1982

[54] ASSAY FOR NEURAMINIC ACIDS

[75] Inventors: Roy E. Snoke; Theodore W. Esders, both of Webster, N.Y.

[73] Assignee: Eastman Kodak Company, Rochester, N.Y.

[21] Appl. No.: 141,748

[22] Filed: Apr. 18, 1980

[51] Int. Cl.³ .......................... C12Q 1/00; C12Q 1/26
[52] U.S. Cl. .......................................... 435/4; 435/18; 435/25; 435/805
[58] Field of Search .................. 23/230 B; 422/56, 57; 424/2, 7; 435/4, 18, 25, 805, 810

[56] References Cited

U.S. PATENT DOCUMENTS

| | | | |
|---|---|---|---|
| 3,901,870 | 8/1975 | Haupt et al. | 435/68 |
| 3,950,322 | 4/1976 | Thomas et al. | 435/18 |
| 3,992,158 | 11/1976 | Przybylowicz | 435/11 |
| 4,042,335 | 8/1977 | Clement | 435/13 |
| 4,246,342 | 1/1981 | Misaki et al. | 435/25 |

OTHER PUBLICATIONS

Burnetti et al. "Enzymatic Determination of Sialic Acid," *Methods of Enzymology,* 6, 1963 pp. 465–473.
Colowick et al. Editors, Methods of Enzymology, vol. 1 pp. 482–490, 1955.

*Primary Examiner*—Peter A. Hruskoci
*Attorney, Agent, or Firm*—Arthur H. Rosenstein

[57] ABSTRACT

A composition and element for assaying a neuraminic acid comprises a neuraminic acid aldolase, pyruvate oxidase and an electron acceptor. A sample containing a neuraminic acid can be contacted with the composition and the product detected spectrophotometrically.

33 Claims, 4 Drawing Figures

ASSAY FOR NEURAMINIC ACIDS

BACKGROUND OF THE INVENTION

1. Field of the Invention

The present invention relates to a method, composition and element for the determination of neuraminic acids in aqueous liquids.

2. Description of the Related Art

Biological fluids from the human body contain various amounts of sialic acids, which are a class of neuraminic acids. These acids are important in cell-to-cell interaction, as hormone receptor sites and as immunodeterminants for cells. Various pathological states, including cancer, have been found to accompany increased serum content of sialic acid.

Recently, a relationship between the level of sialic acid in saliva and the period just prior to ovulation in human females has been found. This indicates a potentially important diagnostic role for the assay of sialic acid.

Various colorimetric chemical methods have been described to measure sialic acid, including resorcinol, orcinol and thiobarbituric acid procedures. These methods are not absolutely specific for sialic acid, however, as other carbohydrates interfere with the color development in these procedures.

A more specific method for assaying for sialic acid is described in Burnetti, Swanson and Roseman, "Methods in Enzymology", 6, pages 465 to 473 (1963). This method comprises submitting a sample to acid hydrolysis to release the sialic acid which is bound to a more complex biological material in the fluid. The freed sialic acid is then reacted with N-acetyl neuraminic acid aldolase to form N-acetyl mannosamine and pyruvate, which is reacted with lactic dehydrogenase (LDH) and reduced nicotinamide adenine dinucleotide (NADH) to measure the resulting decrease in NADH spectrophotometrically at 340 nm. However, N-acetyl neuraminic acid aldolase preparations in the assay contain NADH oxidase which interferes with the assay in that it oxidizes NADH to NAD$\oplus$, thereby introducing a source of positive bias.

Additionally, it is desirable to use dry elements to assay for sialic acid, since a structure containing reactants in a coating would greatly simplify the assay. NADH is quite unstable during coating and storage, is expensive and its limited absorbtivity produces low sensitivity at low analyte levels. Thus, a dry element containing NADH as a reactant would not be advantageously used.

An alternative method for measuring the pyruvate generated by the aldolase (and thus the sialic acid) is highly desirable.

SUMMARY OF THE INVENTION

Figure 1:
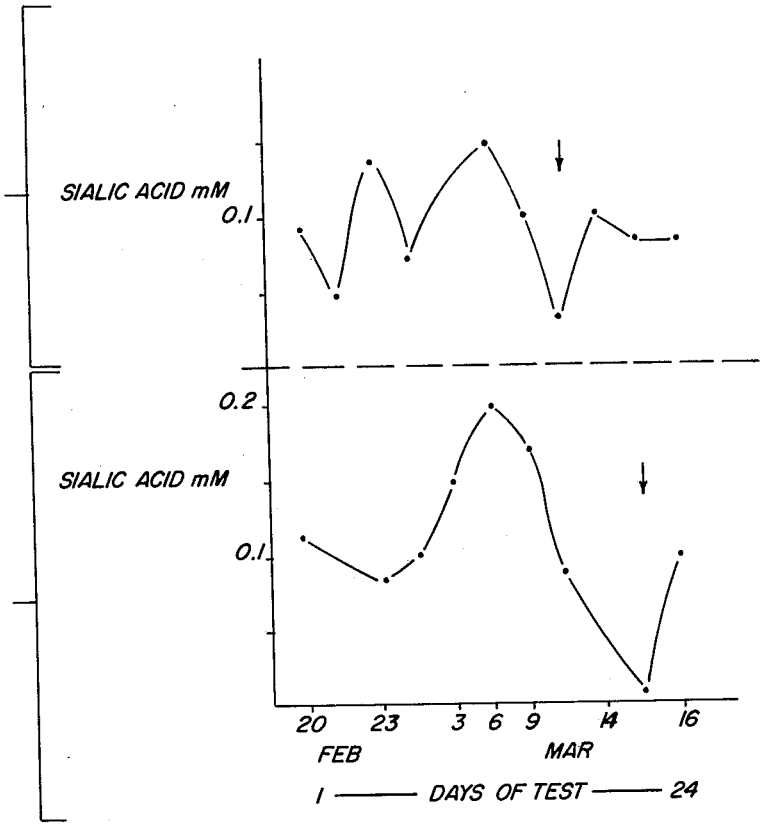
FIGS. 1a and 1b are graphs of sialic acid concentration determination, as related to ovulation.

We have now developed a novel composition, element and method for the assay of neuraminic acids in aqueous liquids, such as blood serum and saliva, which is highly specific, can measure both free and bound neuraminic acids, can be run at relatively low temperatures, has a minimum of interferants and is a continuous method.

This method involves contacting a sample for analysis and a novel assay composition comprising a neuraminic acid aldolase, pyruvate oxidase and an electron acceptor to produce a detectable product and detecting the detectable product.

DESCRIPTION OF THE PREFERRED EMBODIMENTS

A composition useful in assaying for neuraminic acids comprises a neuraminic acid aldolase, pyruvate oxidase and an electron acceptor.

The neuraminic acid aldolases, such as N-acetyl neuraminic acid aldolase and the like, are well known, as are their properties, and are described in Brunetti et al, which was referred to earlier, and in D. G. Comb and S. Roseman, *J. Biol. Chem.*, 235, page 2529 (1960), and P. B. Brunetti, G. W. Jourdian and S. Roseman, *J. Biol. Chem.*, 237, page 2447 (1962).

Pyruvate oxidase can be obtained from many sources, such as animal and microbial. Microbial sources include various species from the family Lactobacillaceae, *Escherichia coli* and the like. In one embodiment the pyruvate oxidase was isolated from *Lactobacillus delbrueckii*, as described in L. P. Hager, B. M. Geller and F. Lippmann, *Federation Proceedings*, 13, pages 734 (1954).

The *Lactobacillus delbrueckii* can be cultured in a composition comprising Difco malt extract, Bacto tryptone, Difco yeast extract, glucose, sodium acetate trihydrate, $MgSO_4.7H_2O$, NaCl, $MnSO_4.4H_2O$ and distilled water at a pH of 6.5.

Various strains of *Lactobacillus delbrueckii* can be used, such as the ATCC 9649 strain, the NRRL-B445 strain, Snell 82-3 and Snell 82-4 strains.

A great variety of electron acceptors can be used in the novel composition. Examples of useful electron acceptors are dichloroindophenol, oxygen, methylene blue, $K_3Fe(CN)_6$, 2-(p-iodophenyl)-3-(p-nitrophenyl)-5-phenyl-2H-tetrazolium chloride, neotetrazolium and the like.

A preferred electron acceptor is a dichloroindophenol. A particularly useful dichloroindophenol is 2,6-dichloroindophenol. The particular electron acceptor used can depend on the strain of the source of pyruvate oxidase, any cofactors used in the composition and other factors. Some electron acceptors which alone would not be highly specific and have good activity for pyruvate oxidase can be used with a cofactor, such as phenazine methosulfate and give excellent results.

Another electron acceptor useful herein is oxygen. The $H_2O_2$ produced as a result of the use of oxygen can be quantified by the color produced by well known peroxidase-coupled reactions.

An "electron acceptor" is defined as a material which is reduced when taking part in the oxidation of another material.

The composition can contain varying amounts of the components, but preferably contains at least 0.1 unit of a neuraminic acid aldolase, at least 0.0005 unit of pyruvate oxidase and from 0.02 millimolar to 10 millimolar of an electron acceptor depending upon the acceptor used.

The composition can contain other materials which can aid in the detection of neuraminic acids, such as surfactants, e.g., Triton X-100 ®; cofactors such as flavin adenine dinucleotide (FAD); thiamine pyrophosphate (TPP); divalent cations such as magnesium; and coupling enzymes such as peroxidase.

The composition can be used either in an aqueous solution or can be used in a dry element. The composition generally contains a buffer, such as potassium phosphate, and tris(hydroxymethyl)aminomethane chloride. In a preferred embodiment, the pH of the composition is buffered to between 5 and 9.

In a preferred embodiment, the composition contains neuraminidase. The neuraminidase will free the blocked or combined neuraminic acids in body fluids. U.S. Pat. No. 3,901,870 describes the use of neuraminidase for biological studies. The neuraminidase is generally present in the composition at a concentration of at least 0.01 unit.

A method of the present invention for the detection of a neuraminic acid comprises the steps of:

(a) contacting, a sample in an aqueous medium, with a composition comprising a neuraminic acid aldolase, pyruvate oxidase and an electron acceptor; and (b) determining the detectable product.

The process can be carried out in an aqueous solution, or it can be carried out in a dry element. The sample containing the unknown amount of a neuraminic acid, when contacted with the neuraminic acid aldolase, reacts to form pyruvate and a mannosamine. The resulting pyruvate reacts with the electron acceptor, preferably a dichloroindophenol or oxygen in the presence of the pyruvate oxidase to form the reduced electron acceptor. The change in color is proportional to the concentration of neuraminic acid in the sample. If dichloroindophenol is the acceptor the color is decreased and if oxygen is used, the color in the system is increased. Thus, the determination of the product is made by calculating the total extent of dye change and correlating that change (increase or decrease) with the amount of a neuraminic acid standard that gave an identical change either by a standard curve or by an acceptor absorbance coefficient.

If the sample to be measured is blood serum or saliva and the neuraminic acid is in the form of sialic acid which is bound to biological materials such as glycoproteins, carbohydrates, glycolipids and the like, the method of this invention can be used to assay for both free and bound sialic acid. In this embodiment, the assaying composition also comprises neuraminidase. The neuraminidase reacts with the bound material to free the sialic acid.

To determine the total amount of both bound sialic acid and free sialic acid, the sample is first assayed using the composition without neuraminidase to determine the concentration of free sialic acid, and the sample is then assayed with the composition containing neuraminidase. The concentration of bound sialic acid is quantified from the difference in determinations.

A dry element useful for assaying neuraminic acid comprises a support having thereon at least one reagent layer containing a neuraminic acid aldolase, pyruvate oxidase and an electron acceptor.

The support comprises any useful material, such as paper and polyolefin-coated paper, as well as a variety of polymeric materials, such as cellulose acetate, poly(ethylene terephthalate), polycarbonates and polyvinyl compounds, such as polystyrenes. Preferred supports include transparent support materials capable of transmitting electromagnetic radiation of a wavelength within the region between about 200 nm and about 900 nm.

The sample is added to the layer in any form, such as in the form of a drop, and the reading is made from either the reagent layer or a separate layer. It is sometimes advantageous to use two reagent layers.

The assay composition is useful in dry chemistry systems. It is, for example, incorporated by imbibition, impregnation or by coating techniques in a reagent zone of a dry test element, e.g., a reagent layer of a dip-and-read fibrous test strip or a reagent layer of a non-fibrous multilayer element, as described in Przybylowicz et al, U.S. Pat. No. 3,992,158, and Clement, U.S. Pat. No. 4,042,335.

The element comprises reagent layers or zones and, optionally, spreading layers or zones. Elements containing these zones and/or layers are described in U.S. Pat. No. 3,992,158, which is hereby incorporated by reference.

The substantially dry element is contacted with a sample for analysis, and the resulting reduced electron acceptor detected. If the initial sample itself is not contained in an aqueous medium, water could be added to the sample prior to adding the sample to the dry element.

A particularly preferred test element for the detection of neuraminic acid in a liquid comprises a support having thereon a spreading layer, a reagent layer and a registration layer in fluid contact under conditions of use. The reagent layer intervenes the spreading layer and the registration layer and the registration layer intervenes the reagent layer and the support. The reagent layer comprises the assaying composition. The registration layer is described in detail in U.S. Pat. No. 4,042,335, columns 11 and 12.

The following examples will serve to better demonstrate the successful practice of the present invention. In the examples, all solutions were prepared with deionized distilled water.

In the following examples sialic acid determinations were performed as follows.

An assay mixture contained in 1.0 ml: 44.0 mM potassium phosphate, pH 7.0, 4.4 mM magnesium chloride, 88.0 mM thiamine pyrophosphate, 53.0 $\mu$M 2,6-dichloroindophenol, 8.8 $\mu$M flavin adenine dinucleotide, 0.03 units neuraminidase, 5.2 milliunits pyruvate oxidase, and sample as indicated in the examples. Tubes were incubated for 5 minutes at 37° C., then 0.1 unit N-acetyl neuraminic acid aldolase was added, an the bleaching of color was followed spectrophotometrically at 600 nm ($\epsilon = 1.6 \times 10^4$).

Example 1—Determination of Sialic Acid in Saliva
(Bound versus Free)

A sample of whole saliva (20 $\mu$l) was assayed as follows.

An assay mixture contained in 1.0 ml; 44.0 mM of potassium phosphate, pH of 7.0, 4.4 mM of magnesium chloride, 88.0 mM of thiamine pyrophosphate (cofactor), 53.0 $\mu$M of 2,6-dichloroindophenol, 8.8 $\mu$M of flavin adenine dinucleotide (cofactor), 5.2 milliunits of pyruvate oxidase, and 20 $\mu$l of sample. The mixture was incubated for 5 minutes at 37° C. and 0.1 unit N-acetyl neuraminic acid aldolase was added. There was no significant change in optical density after 5 minutes of incubation. When 0.03 units of neuraminidase was added to the mixture, the change in optical density was 3.1, indicating a sialic acid content of 1.9 $\mu$moles.

The above shows that essentially all of the salivary sialic acid present was bound (most likely to the mucins produced by the salivary glands). The calculated concentration of sialic acid in this sample was 30 μg/ml.

Example 2—Relation of Sialic Acid Level to Ovulation

It is reported that the sialic acid level in whole saliva decreases just prior to ovulation. Sialic acid concentrations in saliva were determined from two human females. Saliva was supplied every 3 days for 24 days. Approximately 1.0 ml of saliva was collected without stimulation of salination in the morning. The samples were assayed for sialic acid concentration according to the process described above. FIGS. 1a and 1b indicate that an obvious minimum in sialic acid occurred. The minimums were found to have occurred at the midpoint of the menstrual cycle as determined by changes in rectal temperature (1a) or by determining 14 days past onset of menstruation (1b).

Example 3—Compatibility of Components

A. To demonstrate that all components of the assay were compatible and that the enzymes functioned in the mixture, two reaction tubes, each containing the reaction buffer and pyruvate oxidase, were prepared. N-acetyl neuraminic acid aldolase was added to one tube, buffer to the other. After 5 minutes at 37° C., reactions were initiated by adding pyruvate (10 μM) to each tube. As indicated in Table I, initial rates of pyruvate oxidation (expressed as ηmoles per minute) and final optical density changes (O.D.) were identical in each tube with complete oxidation of all pyruvate present. The aldolase, therefore, did not interfere with pyruvate oxidation and did not affect the reduction of 2,6-dichloroindophenol.

TABLE I

|  | Buffer | N-acetyl Neuraminic Acid Aldolase |
|---|---|---|
| ηmoles/min | 3.1 | 3.1 |
| Total O.D. Change | 0.20 | 0.195 |
| Calculated Pyruvate | 12.5 μM | 12.2 μM |

Figure 2:
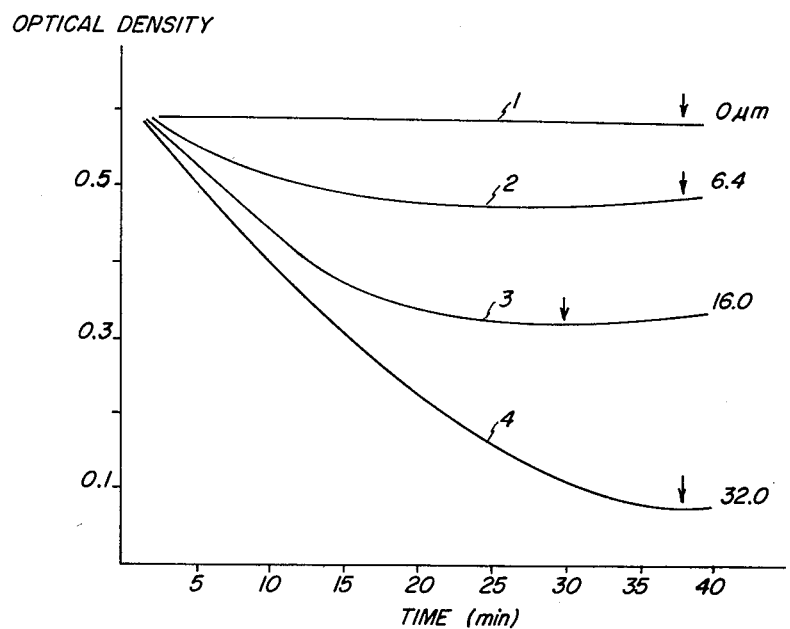
FIG. 2 shows the time curves of assaying reactions at various sialic acid levels.
Figure 3:
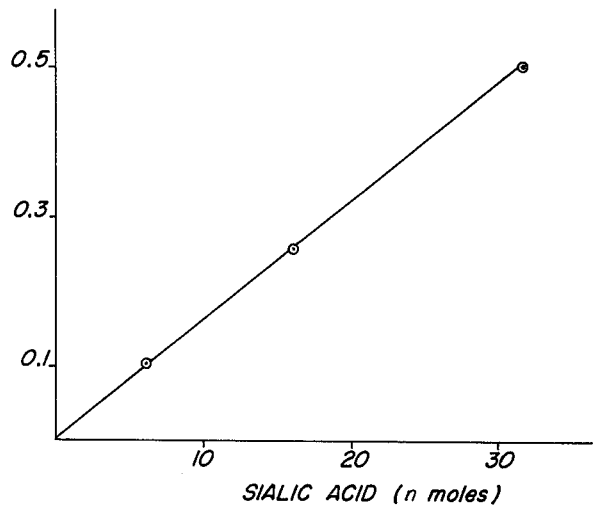
FIG. 3 is a comparison of optical density change with increasing amounts of sialic acid present.

B. When 0.32 μM of sialic acid was added to these tubes, a rapid loss of color was observed only in the tube containing aldolase. Time curves for the analysis of three levels of sialic acid by this coupled system are presented in FIG. 2. Even at the highest concentration tested (32 μM), reaction was completed in less than 40 minutes. (These times could be decreased by increasing the amount of pyruvate oxidase and N-acetyl neuraminic acid aldolase used per assay, or by using less sample.) The optical density changes (i.e., loss of color) observed were directly proportional to the free sialic acid in each tube, as shown in FIG. 3.

Example 4—Determination of Sialic Acid in Human Serum

Samples of pooled human serum were treated as shown in Table II and tested according to the precedure described above. As can be seen in Table II, sialic acid was totally in the bound form, since no reaction occurred in the assay without neuraminidase. Results also indicate that there is no interference from other serum components and, as with salivary sialic acid determinations, both free and bound analyte may be assayed using the same sample.

A slight color reaction was observed with all tubes containing serum, probably due to serum pyruvate (50 to 80 μM is the normal pyruvate level in serum). However, this metabolite did not affect sialic acid assayed by this procedure, because the five-minute incubation prior to starting the reaction with N-acetyl neuraminic acid aldolase was sufficient time for pyruvate oxidase to eliminate this interferent and give a stable baseline value for the assay.

The sialic acid concentration in normal human serum is 1.7 to 2.7 mM.

TABLE II

| Addition to Assay | Sialic Acid |
|---|---|
| 25 μl Serum | 0 |
| 25 μl Serum + 8 μl Sialic Acid* | 4.7 μmoles |
| 25 μl Serum + 25 μl Sialic Acid* | 14.1 |
| 25 μl Sialic Acid | 13.4 |
| 25 μl Serum + Neuraminidase | 18.3 |
| 25 μl Serum + 8 μl Sialic Acid* + Neuraminidase | 21.3 |

*Stock sialic acid solution is 0.64 mM sialic acid

The invention has been described in detail with particular reference to preferred embodiments thereof, but it will be understood that variations and modifications can be effected within the spirit and scope of the invention.

What is claimed is:

1. A composition having a pH of between 5 and 9 comprising at least 0.1 unit neuraminic acid aldolase, at least about 0.005 unit pyruvate oxidase and from about 0.2 millimolar to about 10 millimolar electron acceptor.

2. The composition of claim 1 wherein the neuraminic acid adlolase is N-acetyl neuraminic acid aldolase.

3. The composition of claim 1 wherein the electron acceptor is a dichloroindophenol.

4. The composition of claim 1 wherein the electron acceptor is oxygen.

5. The composition of claim 1 which is aqueous and comprises a buffer.

6. The composition of claim 1 comprising at least 0.01 unit neuraminidase.

7. An aqueous composition having a pH of between 5 and 9 comprising a liquid containing a neuraminic acid, at least 0.1 unit neuraminic acid aldolase, at least about 0.005 unit pyruvate oxidase and from about 0.02 millimolar to about 10 millimolar of an electron acceptor.

8. The composition of claim 7 wherein the neuraminic acid aldolase is N-acetyl neuraminic acid aldolase.

9. The composition of claim 7 wherein the electron acceptor is a dichloroindophenol.

10. The composition of claim 7 wherein the electron acceptor is oxygen.

11. The composition of claim 7 which is aqueous and comprises a buffer.

12. The composition of claim 7 comprising at least 0.01 unit neuraminidase.

13. An aqueous composition having a pH between about 5 and 9 comprising a biological sample containing sialic acid, at least 0.1 unit of N-acetyl neuraminic acid aldolase, at least about 0.005 unit of pyruvate oxidase, from about 0.02 millimolar to about 10 millimolar of a dichloroindophenol and at least about 0.01 unit of neuraminidase.

14. A method for the detection of a neuraminic acid comprising the steps of:

(a) contacting in an aqueous medium a sample for analysis and a composition having a pH between about 5 and 9 comprising at least 0.1 unit of a neuraminic acid aldolase, at least about 0.005 unit pyruvate oxidase and from about 0.02 millimolar to about 10 millimolar of an electron acceptor; and (b) determining the detectable product.

15. The method of claim 14 wherein the neuraminic acid aldolase is N-acetyl neuraminic acid aldolase.

16. The method of claim 14 wherein the electron acceptor is dichloroindophenol.

17. The method of claim 14 wherein the electron acceptor is oxygen.

18. The method of claim 14 wherein said composition is aqueous and comprises a buffer.

19. A method for the detection of a neuraminic acid bound to other biological materials comprising the steps of:

(a) contacting in an aqueous medium a sample for analysis and a composition having a pH between about 5 and 9 comprising at least 0.1 unit of a neuraminic acid aldolase, at least about 0.005 unit pyruvate oxidase, between about 0.02 millimolar to about 10 millimolar of an electron acceptor and at least 0.01 unit neuraminidase; and (b) determining the detectable product.

20. A method for the detection of free and bound neuraminic acids comprising the steps of:

(a) contacting in an aqueous medium a sample for analysis and a composition having a pH between about 5 and 9 comprising at least 0.1 unit of a neuraminic acid aldolase, at least about 0.005 unit pyruvate oxidase and from about 0.02 millimolar to about 10 millimolar of an electron acceptor;

(b) determining any detectable product of (a);

(c) adding to said aqueous medium at least 0.01 unit neuraminidase; and (d) determining the detectable product of (c); and (e) quantifying the amount of free neuraminic acid and bound neuraminic acid from the difference of (b) and (d).

21. The method of claim 20 wherein said neuraminic acid is sialic acid.

22. The method of claim 20 wherein said electron acceptor is dichloroindophenol.

23. The method of claim 20 wherein said electron acceptor is oxygen.

24. An element for the detection of a neuraminic acid comprising a support having thereon at least one reagent layer containing at least 0.1 unit of a neuraminic acid aldolase, at least about 0.005 unit pyruvate oxidase and from about 0.02 millimolar to about 10 millimolar of an electron acceptor.

25. The element of claim 14 comprising two reagent layers, the first reagent layer comprising pyruvate oxidase and an electron acceptor, and the second reagent layer comprising a neuraminic acid aldolase.

26. The element of claim 24 wherein said electron acceptor is a dichloroindophenol.

27. The element of claim 24 wherein said electron acceptor is oxygen.

28. The element of claim 24 wherein said neuraminic acid aldolase is N-acetyl neuraminic acid aldolase.

29. An element for the detection of neuraminic acids bound to other biological materials comprising a support having thereon a composition having a pH between about 5 and 9 comprising at least 0.1 unit of a neuraminic acid aldolase, at least about 0.005 unit pyruvate oxidase, from about 0.02 millimolar to about 10 millimolar of an electron acceptor and at least 0.01 unit neuraminidase.

30. The element of claim 29 wherein said electron acceptor is a dichloroindophenol.

31. The element of claim 29 wherein the electron acceptor is oxygen.

32. An element for the detection of a neuraminic acid in a liquid, the element comprising a support having thereon a spreading layer, at least one reagent layer and a registration layer in fluid contact under conditions of use, the reagent layer intervening the spreading layer and the registration layer, and the registration layer intervening the reagent layer and the support, the reagent layer comprising at least 0.1 unit of a neuraminic acid aldolase, at least about 0.005 unit pyruvate oxidase and from about 0.2 millimolar to about 10 millimolar of an electron acceptor.

33. The element of claim 32 wherein said reagent layer also comprises at least 0.01 unit neuraminidase.

* * * * *

UNITED STATES PATENT AND TRADEMARK OFFICE
CERTIFICATE OF CORRECTION

PATENT NO. : 4,316,954

DATED : February 23, 1982

INVENTOR(S) : Roy E. Snoke and Theodore W. Esders

It is certified that error appears in the above-identified patent and that said Letters Patent are hereby corrected as shown below.

Column 2, line 62, "0.0005" should read ---0.005---.

Column 4, line 49, "an" should read ---and---.

Column 5, line 63, "precedure" should read ---procedure---.

Column 6, line 17, "4.7 µmoles" should read --- 4.7 ηmoles ---; line 36, "adlolase" should read ---aldolase---.

Column 8, line 42, "0.2" should read ---0.02---.

Signed and Sealed this

Fourth Day of May 1982

[SEAL]

Attest:

GERALD J. MOSSINGHOFF

*Attesting Officer*  *Commissioner of Patents and Trademarks*